US011610199B2

(12) United States Patent
Arneault et al.

(10) Patent No.: US 11,610,199 B2
(45) Date of Patent: Mar. 21, 2023

(54) MULTI-TENANT NODE ON A PRIVATE NETWORK OF DISTRIBUTED, AUDITABLE, AND IMMUTABLE DATABASES

(71) Applicant: FuelTrust, Inc., Dickinson, TX (US)

(72) Inventors: Jonathan Arneault, Gulf Breeze, FL (US); Marco Cova, Leiria (PT)

(73) Assignee: FuelTrust, Inc., Dickinson, TX (US)

( * ) Notice: Subject to any disclaimer, the term of this patent is extended or adjusted under 35 U.S.C. 154(b) by 0 days.

(21) Appl. No.: 17/722,759

(22) Filed: Apr. 18, 2022

(65) Prior Publication Data

US 2022/0351197 A1    Nov. 3, 2022

Related U.S. Application Data

(60) Provisional application No. 63/178,294, filed on Apr. 22, 2021.

(51) Int. Cl.
*G06F 16/30*     (2019.01)
*G06Q 20/38*     (2012.01)
(Continued)

(52) U.S. Cl.
CPC ......... *G06Q 20/3825* (2013.01); *G01N 31/00* (2013.01); *G06F 16/27* (2019.01);
(Continued)

(58) Field of Classification Search
CPC ..................................................... G06F 16/27
See application file for complete search history.

(56) References Cited

U.S. PATENT DOCUMENTS

2003/0195708 A1   10/2003   Brown
2004/0019437 A1   1/2004    Kelemen et al.
(Continued)

FOREIGN PATENT DOCUMENTS

WO   2020145887 A2   7/2020
WO   2020/245280 A1  12/2020
WO   2021/250045 A1  12/2021

OTHER PUBLICATIONS

Mar. 5, 2021, IBM Molecule Generation Experience: Supercharging new materials design with AI and Hybrid Cloud, Seiji Takeda.
(Continued)

*Primary Examiner* — Khanh B Pham
(74) *Attorney, Agent, or Firm* — Banner & Witcoff, Ltd.

(57) ABSTRACT

The present disclosure describes a technology platform for creating and updating records of resources in a ledger. To create a record, a tenant organization may prepare a record to write to the ledger that may be flagged as temporary. Metadata may be added to the record, which flags the record as temporary. The metadata may comprise a unique code and an identification of a user that can approve the temporary record. The unique code and the identification may be sent, by the technology platform, to a device associated with one or more approving devices. Upon receiving the code and the identification of the transaction, the device may sign the unique code and invoke a routine based on the identification. The routine may fetch the temporary record. The device may compare the unique code to a code stored in the metadata of the temporary record. Upon valid verification of the unique code, the device may indicate authorization of the write. Based on the authorization, a proxy node associated with the technology platform may write a definitive record to the ledger based on the temporary record.

20 Claims, 9 Drawing Sheets

(51) Int. Cl.
| | |
|---|---|
| *G06Q 20/40* | (2012.01) |
| *G01N 31/00* | (2006.01) |
| *G06N 3/00* | (2023.01) |
| *G06Q 10/08* | (2023.01) |
| *G06F 16/27* | (2019.01) |
| *G06N 5/00* | (2023.01) |

(52) U.S. Cl.
CPC ............ *G06N 3/00* (2013.01); *G06N 5/00* (2013.01); *G06Q 10/08* (2013.01); *G06Q 20/389* (2013.01); *G06Q 20/4014* (2013.01)

(56) References Cited

U.S. PATENT DOCUMENTS

| | | | |
|---|---|---|---|
| 2005/0223004 A1* | 10/2005 | McKenney | G06F 16/10 |
| 2005/0246316 A1 | 11/2005 | Lawson et al. | |
| 2005/0267723 A1 | 12/2005 | Hearn et al. | |
| 2012/0290223 A1 | 11/2012 | Mertens | |
| 2013/0185044 A1 | 7/2013 | Chen et al. | |
| 2014/0231641 A1 | 8/2014 | Qian et al. | |
| 2018/0307803 A1 | 10/2018 | Watanasiri et al. | |
| 2020/0042671 A1 | 2/2020 | Martin et al. | |
| 2020/0104465 A1 | 4/2020 | Martin et al. | |
| 2020/0118117 A1 | 4/2020 | McManus et al. | |
| 2020/0134760 A1* | 4/2020 | Messerges | G06Q 10/04 |
| 2020/0252404 A1 | 8/2020 | Padmanabhan | |
| 2020/0342539 A1 | 10/2020 | Doney | |
| 2020/0349532 A1 | 11/2020 | Brown et al. | |
| 2020/0351094 A1 | 11/2020 | Canterbury et al. | |
| 2021/0256016 A1* | 8/2021 | Gramoli | G06Q 20/389 |
| 2021/0272037 A1 | 9/2021 | Hanebeck | |
| 2021/0390549 A1* | 12/2021 | Rule | H04L 9/0637 |
| 2022/0094692 A1* | 3/2022 | Wolohan, Jr. | G06F 16/27 |
| 2022/0222610 A1 | 7/2022 | Hall et al. | |

OTHER PUBLICATIONS

Jan. 28, 2021, IBM RXN: New AI Model Boosts Mapping of Chemical Reactions., Philippe Schwaller and Teodoro Laino.
Aug. 26, 2020, RoboRXN: Automating Chemical Synthesis, Teodoro Laino.
Apr. 5, 2022, IBM RXN for Chemistry, The free AI Tool in the Cloud for Digital Chemistry.
Jul. 7, 2021, Chemical Reviews, Combining Machine Learning and Computational Chemistry for Predictive Insights into Chemical Systems, John A. Keith, Valentin Vassilev-Galindo, Bingqing Cheng, Stefan Chmiela, Michael Gastegger, Klaus-Robert Muller and Alexandre Tkatchenko.
Jul. 22, 2022—(WO) International Search Report and Written Opinion—PCT/US2022/025194.
Aug. 20, 2020, MDPI "Inventions" Article: Chemical and Physical Analysis of a Petroleum Hydrocarbon Contamination on a Soil Sample to Determine its National Degradation Feasaility by Kuruna Arjoon et al.
Sep. 12, 2022—(WO) International Search Report & Written Opinion—PCT/US2022/025192.
Rezende, M.; Vale, D.; Aguiar, P.; Riehl, C.; Azevedo, D. Application of Full Factorial Design to Evaluate the Effect of Different Variables on the Stability of Biodiesel Diesel Blends under Storage Conditions. Journal of the Brazilian Chemical Society 2017, 28 ( 10), 1966-1974.
Fakhar, S.S.; Liyanage, K. Blockchain Application in Supply Chain Chemical Substance Reporting. In 22nd Cambridge International Manufacturing Symposium; Cambridge, UK, 2018; pp. 1-21.
Linke, O. T.; Kaner, D.; Patra, S.; Kaser, S.; Meuwly, M. High-Dimensional Potential Energy Surfaces for Molecular Simulations: From Empiricism to Machine Learning. Machine Learning: Science and Technology 2020, 1, 013001:1-22.
Wang, L.; Beeson, D.; Akkaram, S.; Wiggs, G. Gaussian Process Meta-Models for Efficient Probabilistic Design in Complex Engineering Design Spaces. In ASME 2005 International Design Engineering Technical Conferences and Computers and Information in Engineering Conference; ASMEDC: Long Beach, California, USA, 2005; vol. vol. 2: 31st Design Automation Conference, Parts A and B, pp. 785-798.
Jul. 19, 2022, Office Action of related U.S. Appl. No. 17/722,906.
2014, de Oliveira, L. P.; Verstraete, J. J.; Kolb, M. Simulating Vacuum Residue Hydroconversion by Means of Monte-Carlo Techniques. Catalysis Today, 220-222, 208-220.
2007, Freund, H.; Walters, C. C.; Kelemen, S. R.; Siskin, M.; Gorbaty, M. L.; Curry, D. J.; Bence, A. E. Predicting Oil and Gas Compositional Yields via Chemical Structure-Chemical Yield Modeling (CS-CYM): Part 1—Concepts and Implementation. Organic Geochemistry, 38 (2), 288-305.
1997, Ohkawa, T.; Sasai, T ; Komada, N.; Murata, S ; Nomura, M. Computer-Aided Construction of Coal Molecular Structure Using Construction Knowledge and Partial Structure Evaluation. Energy & Fuels, 11 (5), 937-944.
2007, Walters, C. C.; Freund, H.; Kelemen, S. R.; Peczak, P.; Curry, D. J. Predicting Oil and Gas Compositional Yields via Chemical Structure-Chemical Yield Modeling (CS-CYM): Part 2—Application under Laboratory and Geologic Conditions. Organic Geochemistry, 38 (2), 306-322.
2015, Wang, H.; Sheen, D. A. Combustion Kinetic Model Uncertainty Quantification, Propagation and Minimization. Progress in Energy and Combustion Science, 47, 1-31.
2010, Verstraete, J.J.; Schnongs, Ph.; Dulot, H.; Hudebine, D. Molecular Reconstruction of Heavy Petroleum Residue Fractions, Chemical Engineering Science, 65 (1), 304-312.

\* cited by examiner

MULTI-TENANT NODE ON A PRIVATE NETWORK OF DISTRIBUTED, AUDITABLE, AND IMMUTABLE DATABASES

CROSS-REFERENCE TO RELATED APPLICATIONS

This application claims priority to U.S. Provisional Patent Application No. 63/178,294, entitled "Multi-Tenant Node on a Private Network of Distributed, Auditable, and Immutable Databases" and filed on Apr. 22, 2021, which is incorporated by reference herein in its entirety.

This application is also related to U.S. application Ser. No. 17/722,906, filed on Apr. 18, 2022 and entitled "Machine-Learning-Based Chemical Analysis," the entirety of which is herein incorporated by reference in its entireties.

FIELD OF THE DISCLOSURE

Aspects of the disclosure generally relate to ledgers and, more specifically to writing and updating data and/or information contained in the ledger.

BACKGROUND OF THE DISCLOSURE

The tracking of resources (e.g., oil, coal, petroleum, chemicals, etc.) from mining to consumption has proven difficult. Moreover, resources may evolve, degrade, or otherwise change over their lifecycle. Thus, there is a need to track resources throughout their lifecycle as they evolve, degrade, and/or change.

BRIEF SUMMARY OF THE DISCLOSURE

The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below. Corresponding apparatus, systems, methods, and computer-readable media are also within the scope of the disclosure.

The present disclosure describes a technology platform that authenticates relationships across a resource's lifecycle, digitally verifies data from shared sources, validates compliance, and identifies potential fraud. The technology platform described herein tracks a resource's lifecycle from when the resource is harvested, extracted, mined, or otherwise sourced, to the point where the resource is destroyed and/or sequestered. In this regard, the technology platform makes use of a ledger (e.g., blockchain, database, immutable database, etc.) to record, update, verify, and validate the resource and any changes that occur to the resource throughout its lifecycle. This provides an immutable record of the resource that allows third parties to comply with regional, national, and/or global regulations related to the resource.

The technology platform described herein may also comprise an artificial intelligence component. The artificial intelligence component may comprise one or more machine learning models configured to review and/or analyze (e.g., identify and/or extract) the records stored in the ledger. The artificial intelligence component may identify the parties and/or processes through analysis of the known or accessible data of the ledger. Moreover, the artificial intelligence component may identify the parties and/or processes via the understood behaviors and physical laws of the resources and/or business process flows. The artificial intelligence component may also authenticate relationships across a resource's lifecycle, digitally verify data from shared sources, validate compliance with laws and regulations, derive and produce valuable results (e.g., information), and/or identify potential fraud. Based on the analysis performed by the artificial intelligence component, the technology platform may generate one or more electronic communications, notifications, alerts, etc. In this regard, the artificial intelligence component may be able to provide full transparency into every touchpoint associated with the resource. By having full transparency into every touchpoint, risk associated with the resource may be reduced, which may reduce costs and/or the environmental impact of the resource.

The features, along with many others, and benefits are discussed in greater detail below.

BRIEF DESCRIPTION OF THE DRAWINGS

The present disclosure is described by way of example and not limited in the accompanying figures in which.

DETAILED DESCRIPTION OF THE DISCLOSURE

In the following description of the various example embodiments, reference is made to the accompanying drawings, which form a part hereof, and in which is shown by way of illustration various example embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. In addition, it is to be understood that the phraseology and terminology used herein are for the purpose of description and should not be regarded as limiting. Rather, the phrases and terms used herein are to be given their broadest interpretation and meaning.

By way of introduction, aspects discussed herein may describe a technology platform that authenticates relationships across a resource's lifecycle, digitally verifies data from shared sources, validates compliance, and/or identifies potential fraud. In this regard, a record of an asset may be created on a ledger (e.g., blockchain, database, immutable database, etc.), for example, when the resource is harvested, mined, extracted, first recovered, or sourced. In this regard, the ledger may be associated with one or more special nodes that host the other ledger(s) information and/or interoperation, for example, as a private ledger, a public ledger, or a hybrid ledger. The one or more special nodes may then act as a proxy (e.g., proxy node) on behalf of one or more tenant organizations to commit (e.g., write) the record to the ledger or ledgers. As used herein, a tenant organization may comprise one or more users that create the record. In particular, the tenant organization may create the record and append an extra signed metadata field to the record to be written. The combination of the record and the metadata field may be referred to as temporary record or a cloned record. The temporary record may be provided to the proxy node, which may send a communication (e.g., digital message, application programmable interface (API) call, file input, asynchronous data communication, synchronous communication, email communication, push notification, etc.) to the other users of the tenant organization. The other users (including computing systems) of the tenant organization may verify (or deny) the temporary record. If a consensus of the other users verifies the temporary record, the proxy node may sign the record and write the record to the ledger (e.g., private ledger, public ledger, or hybrid ledger). By providing a proxy node and consensus from the tenant organization, the technology platform described herein creates a local permission system within a global permission system of the entirety of the ledger.

Figure 1A:
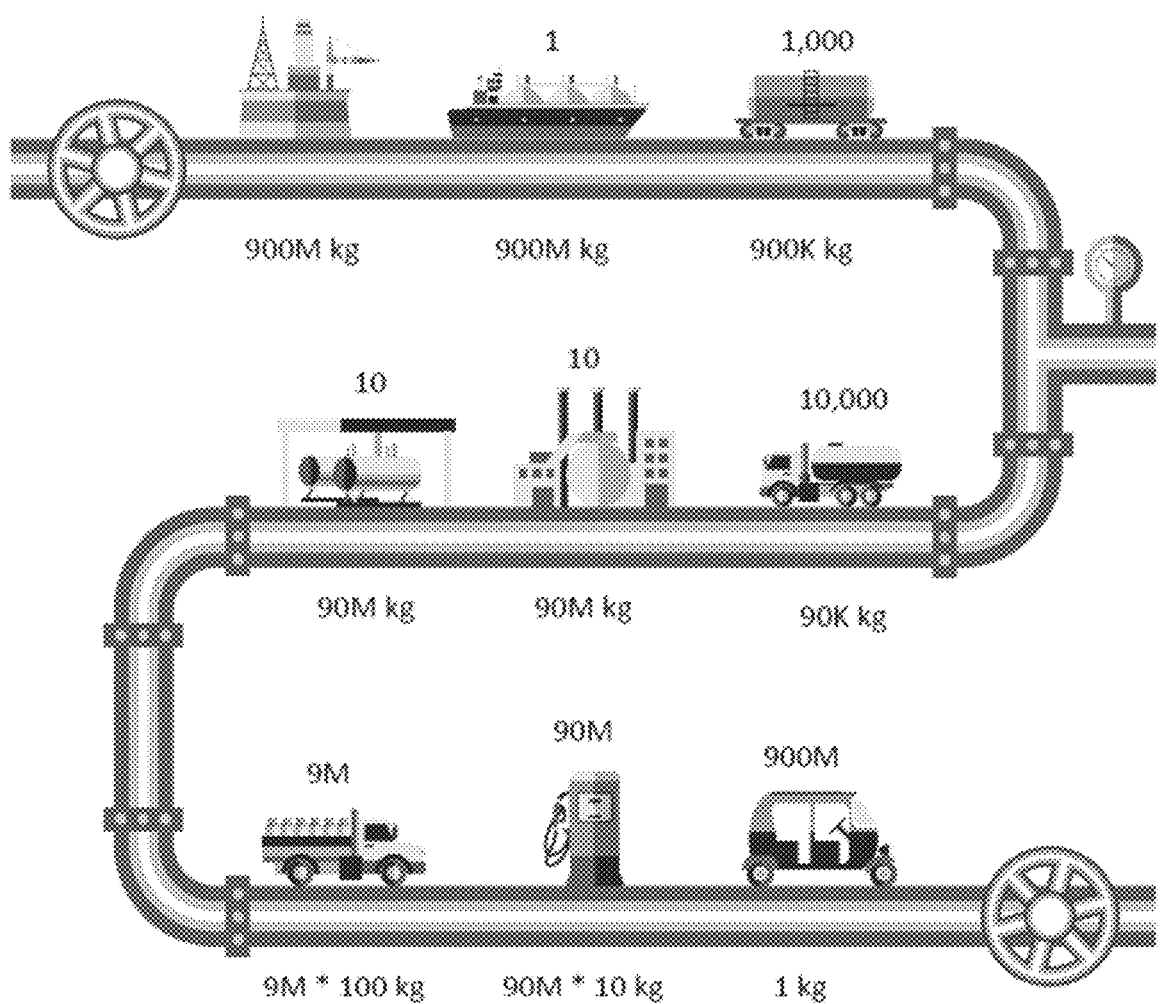
FIGS. 1A-1B show an example of a system for writing and updating data and/or information to a ledger in accordance with one or more aspects of the disclosure.

Turning to FIG. 1A, an example of a lifecycle of a commodity and/or resource is shown. It will be appreciated that commodity and resource may be used interchangeably throughout this disclosure. The resource may comprise a raw material or primary agricultural product. The raw material may be petroleum, coal, oil, chemicals (e.g., such as those used in pharmaceuticals), minerals, metals, or any other fungible resource. It will be appreciated that the lifecycle of any resource may be tracked. The lifecycle of the resource, as shown in FIG. 1A, shows a quantity of containers and/or locations (e.g., offshore derricks, boats, containers, storage tanks, factories, trucks, gas stations, cars) that store the resource at different stages of transportation and/or distribution of the resource and a weight and/or quantity of the resource for each of the containers.

As an example, 900,000,000 kilograms (kg) of petroleum may be extracted at the outset. As will be discussed in greater detail below, a first record of the 900,000,000 kg of petroleum may be created and stored in a ledger. The first record may comprise data and/or information about the 900,000,000 kg of petroleum, including, for example, chemical properties, elemental properties, elemental components, parametric properties, and/or molecular properties of the petroleum, where the petroleum was extracted (e.g., location information), when the petroleum was extracted (e.g., date/time information), etc. The 900,000,000 kg of petroleum may be shipped, for example, from an offshore derrick to a port via a ship. Like the extraction noted above, a second record may be created. The second record may comprise data and/or information, such as an origin of the petroleum, a destination of the petroleum, a shipping route of the petroleum, a length of transit from the origin to the destination, weather conditions at the origin, weather conditions at the destination, weather conditions via the shipping route during the length of transit, etc., in addition to the information discussed above. As will be discussed in greater detail below, one or more applications associated with the technology platform described herein may analyze the data and/or information contained in the second record to determine if any changes occurred to the petroleum (e.g., resource) in transit. If the properties of the petroleum changed while en route, the application may cause a new record to be generated to update the properties of the petroleum. This process may be repeated as the petroleum is shipped by rail and/or truck to a refinery and then distributed to one or more retailers, until the petroleum is consumed (e.g., burned as fuel) or sequestered (e.g., used to manufacture plastics).

Figure 1B:
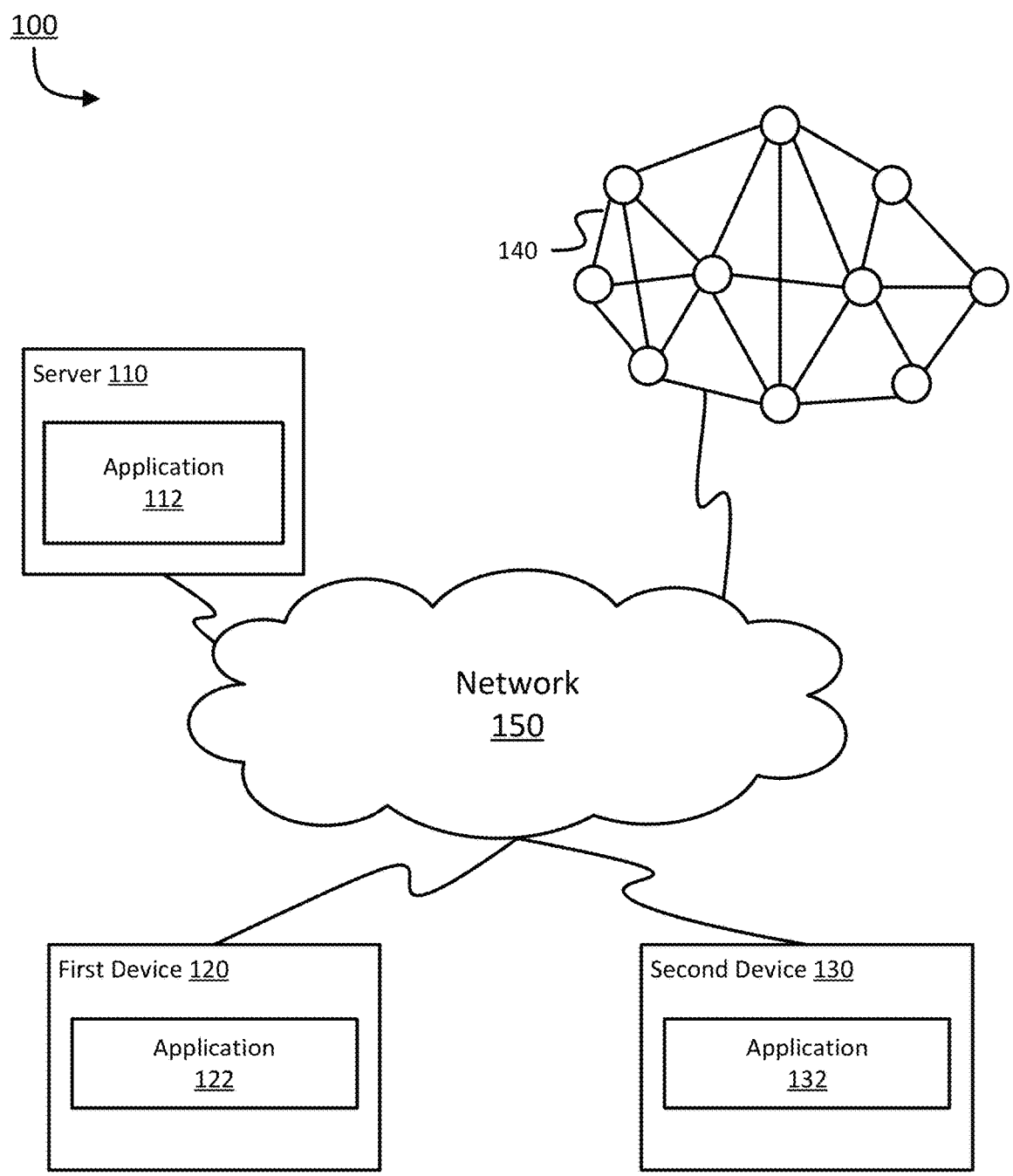

FIG. 1B shows an example of a system 100 comprising a first server 110, a first entity 120, a second entity 130, and a ledger 140 interconnected via a network 150.

Server 110 may be any server capable of executing application 112. In this regard, server 110 may be a stand-alone server, a corporate server, or a server located in a server farm or cloud-computer environment. According to some examples, server 110 may be a virtual server hosted on hardware capable of supporting a plurality of virtual servers. As noted above, server 110 may execute application 112. Application 112 may be server-based software configured to provide or execute a technology platform that authenticates relationships across a resource's lifecycle, digitally verifies data from shared sources, validates compliance, and/or identifies potential fraud. Application 112 may allow one or more tenant organizations to register with the technology platform. A tenant organization may comprise one or more users that create the record to be stored on a ledger, as described in greater detail below with respect to FIG. 6. In this regard, a tenant organization may be a legal or juristic entity that touches, or otherwise comes into contact, with a resource during the resource's lifecycle. The application 112 may receive a record to be written to a ledger, such as the ledger 140, from a computing device associated with a first device associated with the tenant organization. The record may comprise a unique code and a transaction identification. The transaction identifier may indicate a transaction associated with the record. The record may also comprise one or more identifiers associated with one or more second users who are authorized to approve the record. The identifiers may comprise a phone number (e.g., cell phone number), email address, a username, etc. Additionally or alternatively, the record may comprise a different unique code for each of a plurality of approving devices (e.g., devices associated with users authorized to review the record). Upon receiving the record, the application 112 may notify the one or more second users of the tenant organization that the one or more second users have a record for their review. The notification may be sent via an electronic communication, such as digital message, API call, file input, asynchronous data communication, synchronous communication, email communication, push notification, etc. The notification may comprise the unique code and the transaction identifier. The application 112 may receive one or more verifications of the unique code and the transaction identifier from the one or more second users. If a consensus of the one or more second users verify the transaction, the application 112 may write (e.g., commit) the record to the ledger (e.g., ledger 140). The application 112 may sign the record prior to writing the record to the ledger. In this regard, the application 112 may act as a proxy node to create a local permission system within a global permission system of the ledger. Additionally or alternatively, the application 112 may execute a private ledger that allows the record to be validated by the one or more second users. After the record is validated, the application 112 may write (e.g., commit) the record to a public ledger. In some examples, the private ledger and public ledger may form a hybrid ledger accessible by third parties.

Additionally or alternatively, the application 112 may comprise logic that reads and/or writes to the network and/or the ledger 140. The logic may comprise a chemical analysis component that analyzes the chemical composition of the resource, for example, using the process shown in FIGS. 3-5 and described below. As discussed in greater detail below, the logic may consider a variety of factors to determine whether the chemical composition of the resource has changed. Such logic may be comprised of designed algorithms, machine learning algorithms, or machine learning/artificial intelligence algorithms which are derived from human composed algorithms. The variety of factors may comprise one or more of time, temperature, changes in temperature, sedimentation, humidity, light exposure, oxidation, etc. If the chemical composition of the resource has changed, the application 112 may create a new record for the resource that indicates the change to the resource. The chemical composition logic may run periodically (e.g., hourly, daily, weekly, monthly, etc.). Additionally or alternatively, the chemical composition logic may generate an alert, for example, if the change in the chemical composition of the resource presents a danger (e.g., health risk, fire risk, etc.). In some examples, the application 112 may invoke one or more smart contracts on the ledger 140. The one or more smart contracts may record a new record on the ledger 140 or change an existing record on the ledger 140.

The application 112 may also comprise artificial intelligence. The artificial intelligence may comprise one or more machine learning models. The one or more machine learning models may comprise a neural network, such as a convolutional neural network (CNN), a recurrent neural network, a recursive neural network, a long short-term memory (LSTM), a gated recurrent unit (GRU), an unsupervised pre-trained network, a space invariant artificial neural network, a generative adversarial network (GAN), or a consistent adversarial network (CAN), such as a cyclic generative adversarial network (C-GAN), a deep convolutional GAN (DC-GAN), GAN interpolation (GAN-INT), GAN-CLS, a cyclic-CAN (e.g., C-CAN), or any equivalent thereof. Additionally or alternatively, the machine learning model may comprise one or more decisions trees.

The artificial intelligence may be trained to review and/or analyze (e.g., extract) the records stored in the ledger to identify the parties and/or processes, identify relationships between various resources and/or data stored in the ledger, authenticate relationships across a resource's lifecycle, digitally verify data from shared sources, validate compliance with laws and regulations, and/or identify potential fraud. The one or more machine learning models may be trained using supervised learning, unsupervised learning, back propagation, transfer learning, stochastic gradient descent, learning rate decay, dropout, max pooling, batch normalization, long short-term memory, skip-gram, or any equivalent deep learning technique. Once the one or more machine learning models are trained, the one or more machine learning models may be exported and/or deployed in application 112. The application 112 may then analyze and/or review the records in the ledger (such as a blockchain) to reduce the risk associated with one or more resources.

First device 120 may be any device associated with a tenant organization. First device 120 may be a mobile device, such as a cellular phone, a mobile phone, a smart phone, a tablet, a laptop, or an equivalent thereof. Additionally or alternatively, first device 120 may comprise a desktop computer or, alternatively, a virtual computer. First device 120 may provide a first user, associated with a tenant organization, with access to various applications and/or services. For example, first device 120 may provide the first user with access to the Internet. Additionally, first device 120 may provide the first user with one or more applications ("apps") located thereon. The one or more applications may provide the first user with a plurality of tools and access to a variety of services. In some examples, the one or more applications may include an application 122. Application 122 may be a client-based application corresponding to the application 112. In this example, the application 122 may create a record to write to the ledger, for example, as discussed in greater detail below with respect to FIG. 6. The application 122 may flag the record as temporary. Additionally, the application 122 may add metadata to the record. The metadata may comprise the unique code, the transaction identifier, and/or the one or more second users designated to approve the record. In some examples, the application 122 may obfuscate and/or encrypt the metadata. The application 122 may send the record, flagged as temporary, to the server 110. The server may then send the record to the one or more second users identified in the metadata so that the one or more second users can verify (or deny) the record. Additionally or alternatively, the application 122 may receive an indication of one or more records that require review. In this regard, the first device 120 and/or the application 122 may receive a unique code and a transaction identifier of a record that requires review. The application 122 may retrieve the record, for example, using the transaction identifier. The record may be retrieved from the server 110, the application 112, a private ledger (e.g., database) (not shown), the ledger 140, or any combination thereof. Upon receiving the record, the first device 120 (e.g., application 122 executing on first device 120) may compare the unique code with a unique code stored with the record. If the codes match, the application 122 may provide a notification to the server 110 (e.g., the application 112 executing on the server 110) that the record is verified. Similarly, if the codes do not match, the application 122 may provide a notification to the server 110 (e.g., the application 112 executing on the server 110) that the record is not verified. As noted above, the application 112 may track the verifications and, if a consensus (e.g., a predetermined number of approving devices) is reached, write the record to the ledger 140. Additionally or alternatively, the application 122 may invoke one or more smart contracts to record a new record on the ledger 140 or change an existing record on the ledger 140.

The second device 130 may be another device associated with the tenant organization. In this regard, the second device 130 may be any of the devices discussed above with respect to the first device 120. Similarly, the second device 130 may execute application 132, which may provide similar functionality to the functionality described above with respect to the application 122.

The ledger 140 may be any suitable ledger. For example, the ledger 140 may comprise a public blockchain, a private blockchain, a hybrid blockchain, a distributed database, an immutable database, a distributed ledger, etc. The ledger 140 may store the records associated with the one or more resources. Additionally or alternatively, the ledger 140 may store the one or more smart contracts referred to herein. The ledger 140 may be a declarable blockchain. Additionally or alternatively, the ledger 140 may be a discoverable blockchain, wherein interrelationships between blocks of data stored in the ledger 140 may be identified, for example, using recursive analysis of the blocks stored in ledger 140.

The recursive analysis may allow computing devices to perform a forensic analysis of the data contained in the blocks. The forensic analysis may help to identify the source of a resource and/or how the resource has changed or been modified since the resource was originally extracted.

Network 150 may include any type of network. In this regard, the network 150 may include the Internet, a local area network (LAN), a wide area network (WAN), a wireless telecommunications network, and/or any other communication network or combination thereof. It will be appreciated that the network connections shown are illustrative and any means of establishing a communications link between the computers may be used. The existence of any of various network protocols such as TCP/IP, Ethernet, FTP, HTTP and the like, and of various wireless communication technologies such as GSM, CDMA, WiFi, and LTE, is presumed, and the various computing devices described herein may be configured to communicate using any of these network protocols or technologies. The data transferred to and from various computing devices in system 100 may include secure and sensitive data, such as confidential documents, customer personally identifiable information, and account data. Therefore, it may be desirable to protect transmissions of such data using secure network protocols and encryption, and/or to protect the integrity of the data when stored on the various computing devices. For example, a file-based integration scheme or a service-based integration scheme may be utilized for transmitting data between the various computing devices. Data may be transmitted using various network communication protocols. Secure data transmission protocols and/or encryption may be used in file transfers to protect the integrity of the data, for example, File Transfer Protocol (FTP), Secure File Transfer Protocol (SFTP), and/or Pretty Good Privacy (PGP) encryption. In many embodiments, one or more web services may be implemented within the various computing devices. Web services may be accessed by authorized external devices and users to support input, extraction, and manipulation of data between the various computing devices in the system 100. Web services built to support a personalized display system may be cross-domain and/or cross-platform, and may be built for enterprise use. Data may be transmitted using the Secure Sockets Layer (SSL) or Transport Layer Security (TLS) protocol to provide secure connections between the computing devices. Web services may be implemented using the WS-Security standard, providing for secure SOAP messages using XML encryption. Specialized hardware may be used to provide secure web services. For example, secure network appliances may include built-in features such as hardware-accelerated SSL and HTTPS, WS-Security, and/or firewalls. Such specialized hardware may be installed and configured in system 100 in front of one or more computing devices such that any external devices may communicate directly with the specialized hardware.

Figure 2:
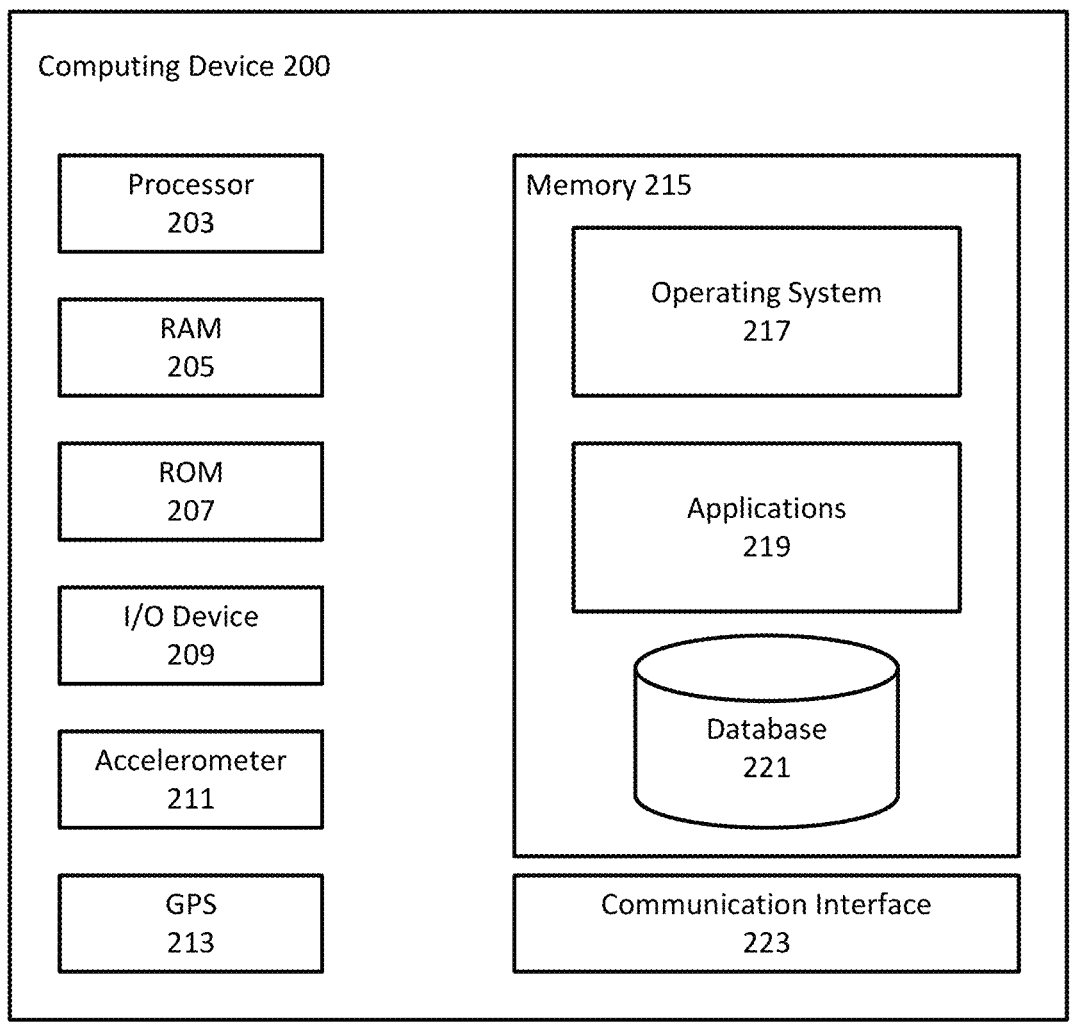
FIG. 2 shows an example of a computing device in accordance with one or more aspects of the disclosure.

Any of the devices and systems described herein may be implemented, in whole or in part, using one or more computing devices described with respect to FIG. 2. Turning now to FIG. 2, a computing device 200 that may be used with one or more of the computational systems is described. The computing device 200 may comprise a processor 203 for controlling overall operation of the computing device 200 and its associated components, including RAM 205, ROM 207, input/output device 209, accelerometer 211, global-position system antenna 213, memory 215, and/or communication interface 223. A bus 202 may interconnect processor(s) 203, RAM 205, ROM 207, memory 215, I/O device 209, accelerometer 211, global-position system receiver/antenna 213, memory 215, and/or communication interface 223. Computing device 200 may represent, be incorporated in, and/or comprise various devices such as a desktop computer, a computer server, a gateway, a mobile device, such as a laptop computer, a tablet computer, a smart phone, any other types of mobile computing devices, and the like, and/or any other type of data processing device.

Input/output (I/O) device 209 may comprise a microphone, keypad, touch screen, and/or stylus through which a user of the computing device 200 may provide input, and may also comprise one or more of a speaker for providing audio output and a video display device for providing textual, audiovisual, and/or graphical output. Software may be stored within memory 215 to provide instructions to processor 203 allowing computing device 200 to perform various actions. For example, memory 215 may store software used by the computing device 200, such as an operating system 217, application programs 219, and/or an associated internal database 221. The various hardware memory units in memory 215 may comprise volatile and nonvolatile, removable and non-removable media implemented in any method or technology for storage of information such as computer-readable instructions, data structures, program modules, or other data. Memory 215 may comprise one or more physical persistent memory devices and/or one or more non-persistent memory devices. Memory 215 may comprise random access memory (RAM) 205, read only memory (ROM) 207, electronically erasable programmable read only memory (EEPROM), flash memory or other memory technology, optical disk storage, magnetic cassettes, magnetic tape, magnetic disk storage or other magnetic storage devices, or any other medium that may be used to store the desired information and that may be accessed by processor 203.

Accelerometer 211 may be a sensor configured to measure accelerating forces of computing device 200. Accelerometer 211 may be an electromechanical device. Accelerometer may be used to measure the tilting motion and/or orientation computing device 200, movement of computing device 200, and/or vibrations of computing device 200. The acceleration forces may be transmitted to the processor to process the acceleration forces and determine the state of computing device 200.

GPS receiver/antenna 213 may be configured to receive one or more signals from one or more global positioning satellites to determine a geographic location of computing device 200. The geographic location provided by GPS receiver/antenna 213 may be used for navigation, tracking, and positioning applications. In this regard, the geographic may also include places and routes frequented by the first user.

Communication interface 223 may comprise one or more transceivers, digital signal processors, and/or additional circuitry and software, protocol stack, and/or network stack for communicating via any network, wired or wireless, using any protocol as described herein.

Processor 203 may comprise a single central processing unit (CPU), which may be a single-core or multi-core processor, or may comprise multiple CPUs. Processor(s) 203 and associated components may allow the computing device 200 to execute a series of computer-readable instructions (e.g., instructions stored in RAM 205, ROM 207, memory 215, and/or other memory of computing device 215, and/or in other memory) to perform some or all of the processes described herein. Although not shown in FIG. 2, various elements within memory 215 or other components in computing device 200, may comprise one or more caches, for example, CPU caches used by the processor 203, page caches used by the operating system 217, disk caches of a hard drive, and/or database caches used to cache content from database 221. A CPU cache may be used by one or more processors 203 to reduce memory latency and access time. A processor 203 may retrieve data from or write data to the CPU cache rather than reading/writing to memory 215, which may improve the speed of these operations. In some examples, a database cache may be created in which certain data from a database 221 is cached in a separate smaller database in a memory separate from the database, such as in RAM 205 or on a separate computing device. For example, in a multi-tiered application, a database cache on an application server may reduce data retrieval and data manipulation time by not needing to communicate over a network with a back-end database server. These types of caches and others may provide potential advantages in certain implementations of devices, systems, and methods described herein, such as faster response times and less dependence on network conditions when transmitting and receiving data.

Although various components of computing device 200 are described separately, functionality of the various components may be combined and/or performed by a single component and/or multiple computing devices in communication without departing from the disclosure.

Generating a Digital Twin Corresponding to a Resource

Figure 3:
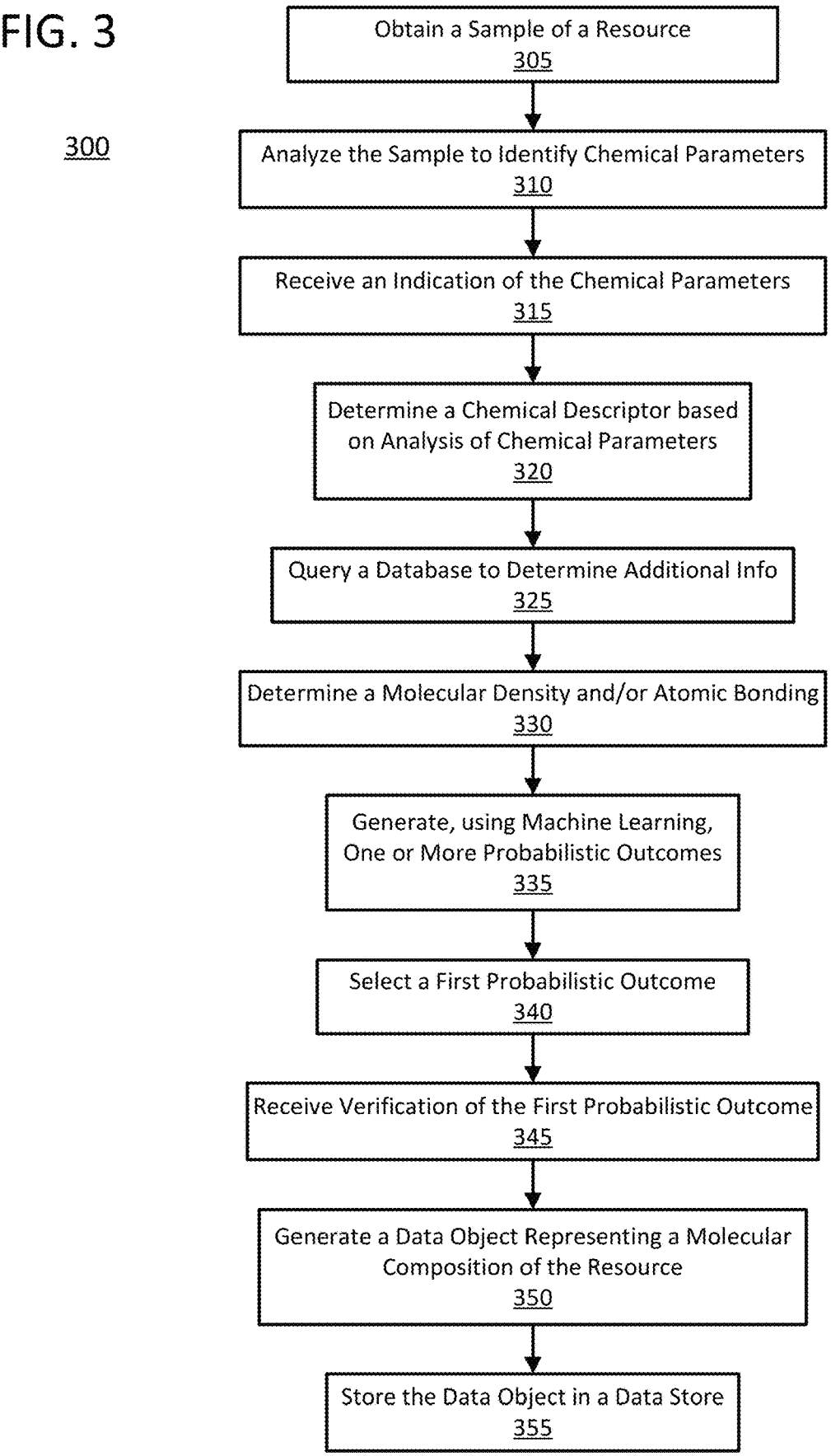
FIG. 3 shows an example of creating a digital representation of a resource in accordance with one or more aspects of the disclosure.

In order to be able to track the evolution of a resource throughout its lifecycle, a digital representation of the resource may be generated. FIG. 3 shows an example of creating a digital representation of a resource in accordance with one or more aspects of the disclosure. Some or all of the steps of process 300 may be performed using one or more computing devices as described herein, including, for example, the server 110, the first device 120, the second device, the computing device 200, or any combination thereof.

In step 305, a sample of a resource may be obtained. The sample may be a physical sample of the resource. With reference to FIG. 1A, the sample may be petroleum. The sample may be obtained at any of the points illustrated in FIG. 1A. For instance, a first sample may be obtained when the petroleum is extracted at the derrick and a second sample may be obtained when the petroleum is loaded onto a ship. In another example, the sample may be a core sample obtained, for example, during mining operations. Once the sample is obtained, the sample may be sent to a laboratory or processing site for further analysis as shown in step 310. The analysis may be used to determine one or more chemical properties, elemental properties, elemental components, parametric components, and/or molecular components associated with the sample. Any methodology or chemical analysis may be performed on the sample. In particular, the analysis techniques may include chromatography and/or mass spectrometry analysis. Preferably, the analysis techniques include gas chromatography-mass spectrometry (GC-MS), liquid chromatography-mass spectrometry (LC-MS), or any equivalent analysis methodology thereof. In some instances, the analysis may warrant a secondary analysis of the sample, for example, if errors are detected or the results are not clear. Based on the analysis, a report may be prepared indicating one or more chemical properties, elemental properties, elemental components, parametric components, and/or molecular components associated with the sample.

In step 315, a computing device may receive the report. The report may include an indication of one or more chemical properties, elemental properties, elemental components, parametric components, and/or molecular components associated with the resource. In particular, the report may include a molecular descriptor for each molecule and/or compound found in the resource, a percentage of each molecular descriptor, a density of each molecular descriptor, and/or any other pertinent information obtained as a result of the analysis performed in step 310. The molecular descriptor may be in the form of a molecular formula, an empirical formula, a Simplified Molecular Input Line Entry System (SMILES), or a structural formula. The molecular formula may represent the elemental components, and their respective number of atoms, that form a single molecule. As an example, the molecular formula for glucose is: $C_6H_{12}O_6$. The empirical formula may represent the elemental components and their ratio of atoms that form a single molecule. The empirical formula for glucose is: CH2O. The SMILES representation may represent the elemental components in the order they pair, with the strength of the atomic bond (e.g., ionic, protonic) represented, and/or their bonding structure (such as rings, arrays, etc.). The SMILES representation for glucose is: OC[C@@H](O1)[C@@H](O)[C@H](O)[C@@H](O)[C@H](O)1. The structural formula may describe the elemental components and/or their bonds. Additionally, the structural formula may describe the atomic distance and/or angle of atoms to one another. Variations of the structural formula may allow for more data to be visually derived, such as ionic and/or protonic attraction or strength, including chemical state. The structural formula for glucose may be represented as:

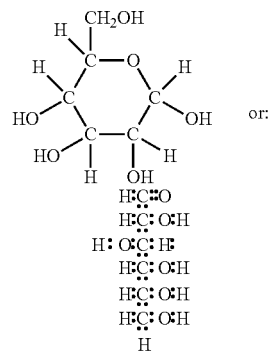

In step 320, the computing device may analyze the report. The report may be analyzed using one or more natural language processing algorithms. The one or more natural language processing algorithms may identify a chemical descriptor associated with the molecular descriptor. As used herein, a chemical descriptor, which may be used interchangeably with compound descriptor, may be a composite of one or more molecular descriptors contained in the report. In this regard, individual molecules may be segregated from one another by a separator, such as a comma, plus sign, bar, etc., and the entire compound may be identified as a unit via a compound separator, such as a bracket, quotation marks, double bars, etc. The one or more natural language processing algorithms may identify the chemical descriptor, for example, based on the molecular descriptors contained therein, the separators, and/or the compound separators. Additionally, the one or more natural language processing algorithms may determine additional information contained in the report, such as a percentage of each molecular descriptor, a density of each molecular descriptor, and/or any other relevant information. Based on the analysis, the computing device may identify data and/or information associated with the resource. Additionally, the computing device may identify gaps (e.g., missing data and/or information) in the report.

Based on any identified gaps, the computing device may query a database to determine additional information associated with the chemical descriptor, in step 325. The database may be a chemistry knowledgebase. The chemistry knowledgebase may include an atomic weight, atomic details, magnetic bonding, electrical bonding, compound information, reactivity information, statefulness, and/or environmental behavior. Accordingly, the computing device may query the database (e.g., chemistry knowledgebase) to fill in the identified gaps. In some examples, the chemistry knowledgebase may also include behavioral components, such as the boiling point of certain compounds. The behavior components may be known and/or discoverable properties of elements and compounds and complex compounds.

In step 330, the computing device may determine a molecular density and/or atomic bonding for the chemical descriptor. The molecular density and/or atomic bonding may be determined using one or more machine learning models. As noted above, the one or more machine learning models may comprise a neural network, such as a CNN, a recurrent neural network, a recursive neural network, a LSTM, a GRU, an unsupervised pre-trained network, a space invariant artificial neural network, a GAN, or a CAN, such as C-GAN, DC-GAN, GAN-INT, GAN-CLS, C-CAN, or any equivalent thereof. Additionally or alternatively, the one or more machine learning model may comprise one or more decisions trees. The one or more machine learning models may be trained to determine the molecular density and/or atomic bonding, for example, based on the data and/or information contained in the report, as well as the additional information obtained from the database (e.g., chemistry knowledgebase).

In step 335, the computing device may generate a plurality of probabilistic outcomes for the resource. The plurality of probabilistic outcomes may be generated using one or more machine learning models, which may be the same machine learning models used to determine the molecular density and/or atomic bonding, Alternatively, one or more second machine learning models, different from those used to determine the molecular density and/or atomic bonding, may be used to determine the plurality of probabilistic outcomes. The plurality of probabilistic outcomes may be based on the information contained in the report, the additional information obtained from the database (e.g., chemistry knowledgebase), the molecular density, and/or the atomic bonding. In some examples, the one or more machine learning models may determine a likelihood percentage for each of the plurality of probabilistic outcomes. That is, the one or more machine learning models may identify a probability that the resource is the chemical compound associated with the probabilistic outcome. In step 340, the computing device may select a first probabilistic outcome as being representative of the resource. The selection may be based on the likelihood percentage associated with each of the plurality of probabilistic outcome. For example, the selection may be based on the highest likelihood percentage. Additionally or alternatively, the selection may be based on the likelihood percentage satisfying a predetermined threshold. In some examples, the computing device may transmit the plurality of probabilistic outcomes to a second computing device and receive a selection of the probabilistic outcome from the second computing device. In some examples, the computing device may send the selection of the first probabilistic outcome to a second computing device (e.g., a client device) with a request to verify the selection. In step 345, the computing device may receive verification that the selection of the first probabilistic outcome was accurate (e.g., correct). It will be appreciated that step 345 may be skipped in some examples.

In step 350, the computing device may generate a data object to represent a molecular composition of the resource, for example, based on a selection of the first probabilistic outcome. The data object may be a chemical digital twin of the resource. As used herein, a "chemical digital twin" is a data object that represents the resource's molecular composition at the state and/or time the sample was taken. In this regard, the chemical digital twin may be an artificially-intelligent generated compound descriptor, as well as the data extracted and/or derived from the source information and/or the sample analysis. In other words, the computing device may take what is known about the resource, the additional information obtained from a knowledgebase, and the possible outcomes of the resource to create a digital twin of the resource. As will be discussed in greater detail below, this digital twin may allow computing devices to track the evolution of a resource throughout its lifecycle. This evolution may include changes that occur as a result of environmental conditions, such as time, temperature, humidity, sun exposure, etc. Additionally or alternatively, this evolution may occur as a result of custodial actions taken by the owner of the resource. For example, the changes in the resource may occur due to preservatives and/or additives being introduced to the resource. In another example, changes in the resource may occur during transfer of ownership when the resource is mixed with residual compounds, such as those found in a storage tank or a fuel barge. Each of these changes may be determined using the techniques described above in FIG. 3, as well as discovered using the machine learning techniques described herein.

In step 355, the computing device may store the data object in a data store. The data store may be a database, a data warehouse, a data lake, or a ledger, such as the ledger 140 discussed above with respect to FIG. 1B. After the digital object is stored, a computing device may compare the data object to a plurality of data objects stored in the distributed ledger to determine whether the data object is related to any of the plurality of data objects. That is, the computing device may analyze the data object to determine whether the data object is related to any of the plurality of other data objects. This analysis may help determine the resource's origin, source, and/or history (e.g., whether the data object is derivative of another data object). The computing device may identify any potential relationships between the data objects in the data store and the probabilities associated with each potential relationship. The potential relationships and their associated probabilities may then be recorded. Furthermore, this analysis may determine the evolution of a resource as it progresses through its lifecycle.

Figure 4:
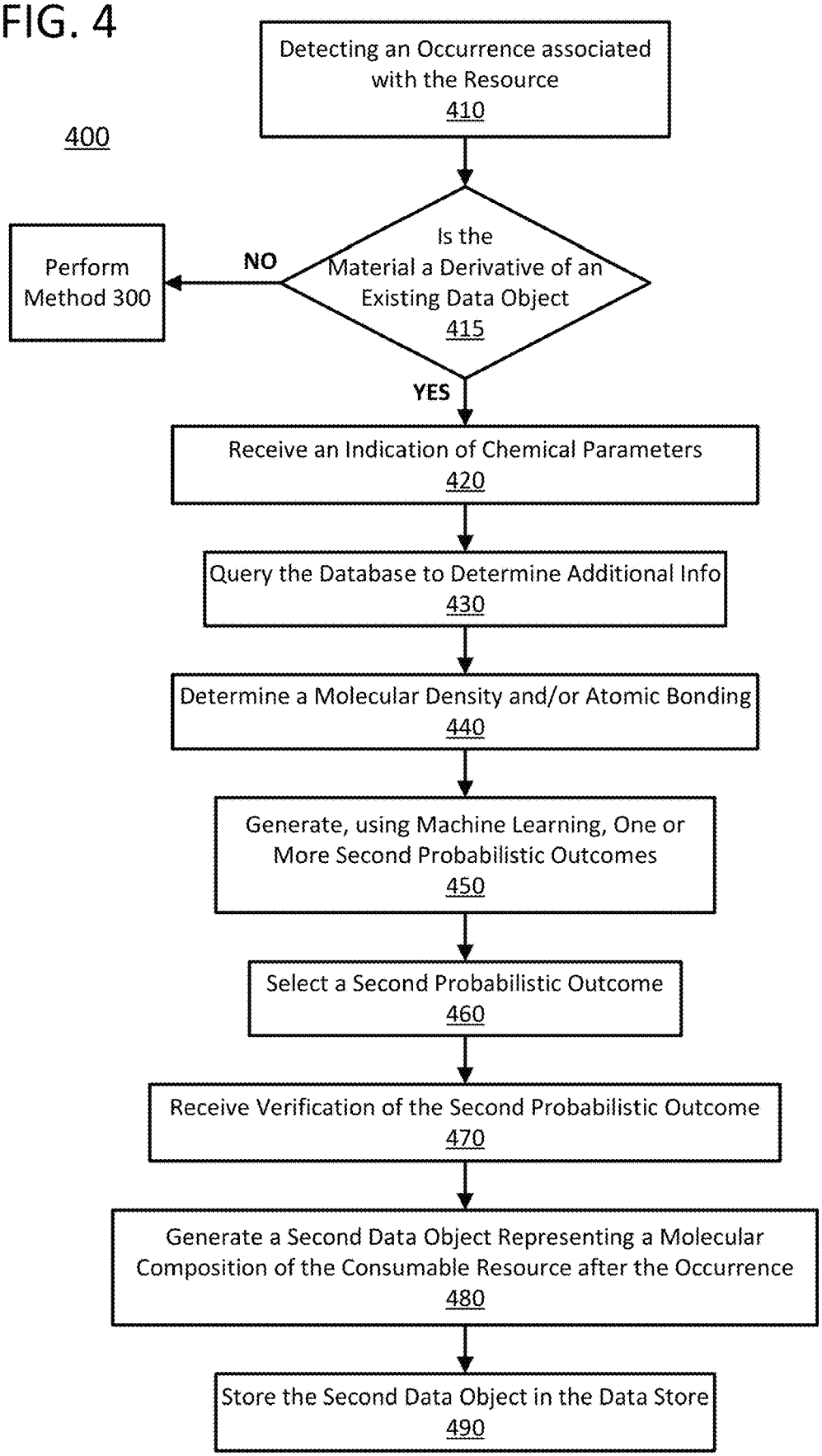
FIG. 4 shows an example of updating a digital representation of a resource in response to a custodial or environmental event according to one or more aspects of the disclosure.

As noted above, the chemical and/or molecular composition of a resource may change over the course of its lifecycle due to custodial or environmental events. FIG. 4 shows an example of updating a digital representation of a resource in response to a custodial or environmental event according to one or more aspects of the disclosure. Some or all of the steps of process 400 may be performed using one or more computing devices as described herein, including, for example, the server 110, the first device 120, the second device, the computing device 200, or any combination thereof.

In step 410, a computing device may detect an occurrence associated with the resource. The occurrence may be a custodial event or environmental event. A custodial event may include a change of ownership and/or transferring the resource from one container to another, such as offloading from a ship onto railcars. In some instances, the occurrence may be a probabilistic recursion of environmental and/or reactive changes as described in greater detail below with respect to FIG. 5. That is, the computing device may be executing a recursive loop to determine whether environmental and/or reactive changes have caused any changes to the resource as represented by a data object. As part of the recursive analysis, the computing device may evaluate a variety of factors, for example, using the one or more machine learning models described herein. The factors may include one or more of time, temperature, sedimentation, humidity, light exposure, oxidation, etc. of the resource, how it was stored, where it was stored, etc. The chemical composition analysis may be performed periodically (e.g., hourly, daily, weekly, monthly, etc.). Periodic analysis of the chemical properties, elemental properties, elemental components, parametric properties, and/or molecular properties of the resource may be performed more frequently, for example, if the resource is being transported.

In step 420, the computing device may determine whether the resulting material is derivative of an existing data object. If the material is not a derivative of an existing data object, then the computing device performs the process 300, described in FIG. 3. However, if the material is a derivative of an existing data object, then the process 400 may proceed to step 430, with the computing device receiving an indication of chemical parameters. Step 430 may be similar to step 315 described above with the computing device receiving a report from a laboratory or testing site. Alternatively, the chemical parameters may be generated as part of the recursive analysis being performed by the computing device. That is, the computing device may generate updated chemical parameters based on the analysis described above and bypass the need for a laboratory and/or testing site to analyze the material.

In step 430, the computing device may query the database to determine additional information associated with the material and the chemical descriptors associated therewith, similar to step 325 described above. In step 440, the computing device may determine a molecular density and/or atomic bonding for the chemical descriptor using the techniques described above with respect to step 330. In step 450, the computing device may generate a second plurality of probabilistic outcomes for the resource, using the one or more machine learning models. In step 460, the computing device may select a second probabilistic outcome as being representative of changes to the resource. In step 470, the computing device may receive verification of the selection of the second data object. The computing device may then generate a second data object to represent an updated molecular composition of the resource in step 480. Finally, in step 490, the computing device may store the second data object in a data store, such as a distributed ledger. When there is a relationship between the first data object and the second data object, the computing device may update the identifiers associated with both data objects to show the interrelationship. Additionally or alternatively, storing the second data object in a data store may include updating the first data object to reflect the changes to the resource.

Figure 5:
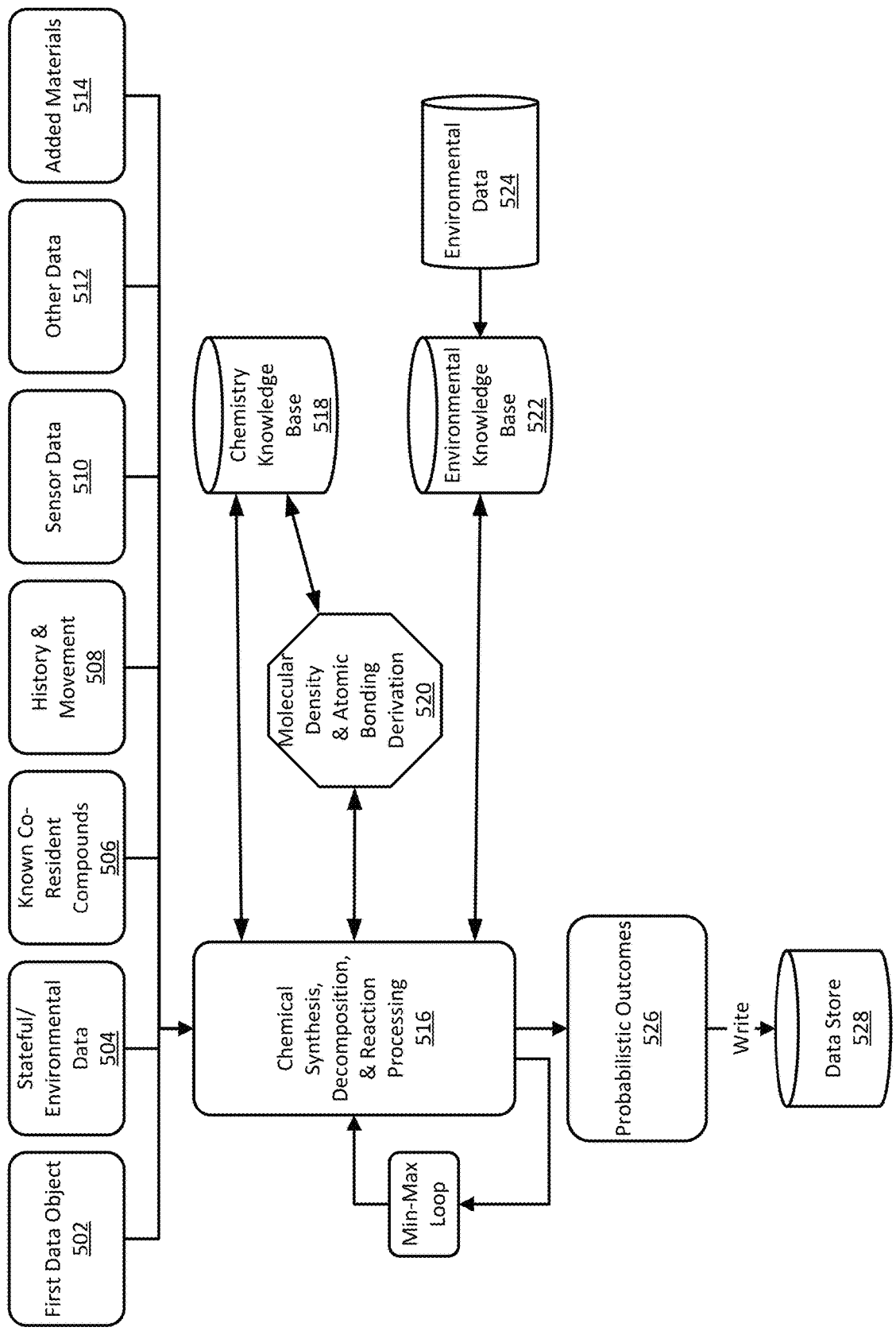
FIG. 5 shows an example of the recursive analysis in accordance with one or more aspects of the disclosure.

FIG. 5 shows an example of the recursive analysis described above to detect the environmental and/or reactive changes of a resource in accordance with one or more aspects of the disclosure. The recursive analysis shown in FIG. 5 may be performed using one or more computing devices as described herein, including, for example, the server 110, the first device 120, the second device, the computing device 200, or any combination thereof.

As part of the recursive analysis, the computing device may analyze the first data object 502, stateful/environmental data 504, known co-resident compounds 506, history and movement data 508, sensor data 510, other data 512, and/or added materials 514. As noted above, the first data object 502 may be a digital twin of the resource that is a chemical and/or molecular representation of the resource. The stateful/environmental data 504 may comprise information about the container and/or environment in which the resource is being stored. In this regard, the stateful/environmental data 504 may identify whether the resource is being stored or in-transit. Additionally, if the resource is in-transit, the stateful/environmental data 504 may indicate how the resource is being transported (e.g., land, sea, air). The known co-resident compounds 506 may indicate residual materials in the container when the resource was introduced to the container. For example, leftover fuel may not be cleaned out from a fuel bunker. The history and movement data 508 may indicate origin of the resource, a destination of the resource, a shipping route of the resource, a length of transit for each segment of the journey, weather conditions at the origin, weather conditions at the destination, weather conditions via the shipping route during the length of transit, etc. The sensor data 510 may include data obtained from one or more sensors associated with the container storing the resource. The one or more sensors may measure temperature, humidity, light, etc. The other data 512 may include any miscellaneous information derived by the computing device, the containers, the sensors, etc. Finally, the added materials 514 may indicate any additional compounds (e.g., additives, preservatives, etc.) that have been introduced to the resource.

The first data object 502, stateful/environmental data 504, known co-resident compounds 506, history and movement data 508, sensor data 510, other data 512, and/or added materials 514 may be used as inputs to a Chemical Synthesis, Decomposition, and Reaction Processing Engine 516. Chemical Synthesis, Decomposition, and Reaction Processing Engine 516 may be the one or more machine learning algorithms described above. In this regard, the Chemical Synthesis, Decomposition, and Reaction Processing Engine 516 may determine what is known and unknown about the resource. Based on the known data, the Chemical Synthesis, Decomposition, and Reaction Processing Engine 516 may derive the unknowns. In order to derive the unknowns, the Chemical Synthesis, Decomposition, and Reaction Processing Engine 516 may query the chemistry knowledgebase 518 to determine an atomic weight, atomic details, magnetic bonding, electrical bonding, compound information, reactivity information, statefulness, and/or environmental behavior with the resource. The computing device may employee a molecular density and/or atomic bonding data engine 520 to derive the molecular density and/or atomic bonding of the molecules and/or compounds contained in the resource. Finally, an environmental knowledgebase 522 may be used to determine how the molecules and/or compounds contained in the resource react to different environmental conditions. Further, the environmental knowledgebase may base the determinations on real-time, or near real-time, environmental data 524. The Chemical Synthesis, Decomposition, and Reaction Processing Engine 516 may receive these additional inputs to generate a plurality of probabilistic outcomes 526. In some examples, the Chemical Synthesis, Decomposition, and Reaction Processing Engine 516 may comprise a loop function (e.g., Min-Max Loop) to limit the number of probabilistic outcomes. The plurality of probabilistic outcomes may be written to data store 528. Alternatively, one of the plurality of probabilistic outcomes may be written to data store 528.

By generating a digital twin of the resource using the techniques described herein, the chemical properties, elemental properties, elemental components, parametric components, and/or molecular components of commodities may be represented in a digital form that accurately tracks the resource throughout its lifecycle and how it may change due to environmental conditions, storage conditions, and/or custodial changes. Moreover the digital twin of the of the resource may be used to generate a non-fungible token. The non-fungible token may be used as part of a carbon offsetting and/or abatement program to represent a carbon credit program that allows entities to buy, sell, or trade carbon credits.

Creating Immutable Records Based on the Digital Twin of the Resource

Figure 6:
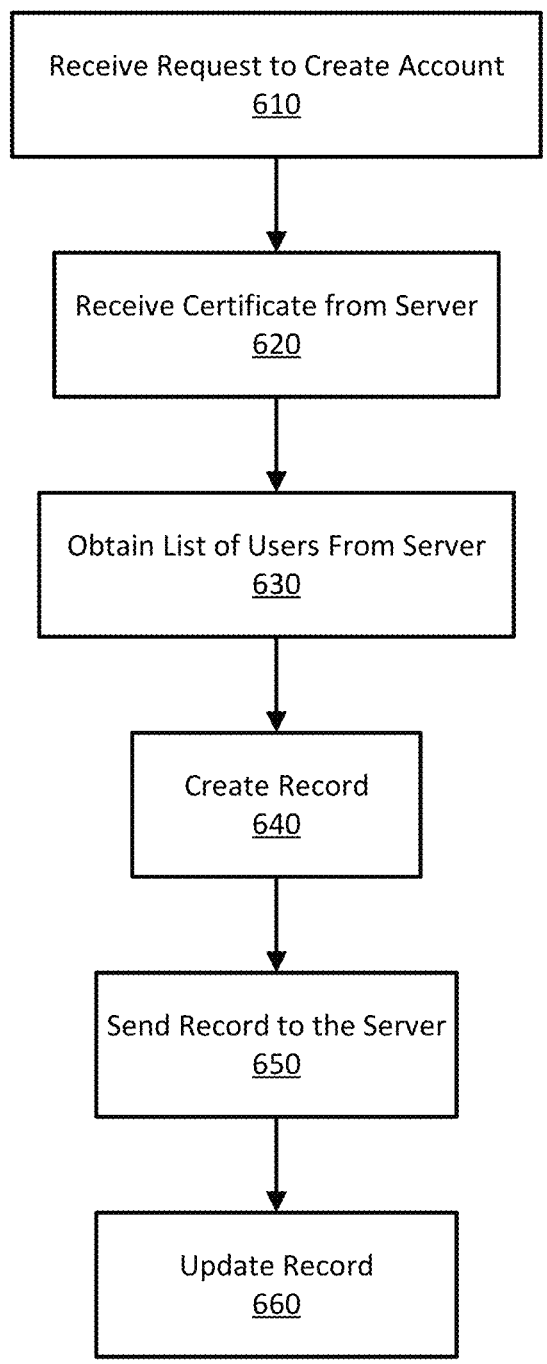
FIG. 6 shows an example of a process of creating a record in accordance with one or more aspects of the disclosure.

In order to be able to track the lifecycle of a resource and use the digital representation, records may be created and stored, for example, in a ledger, that would allow third parties to verify the resource and information associated therewith. FIG. 6 shows an example of a process 600 of creating a record in accordance with one or more aspects of the disclosure. Some or all of the steps of process 600 may be performed using one or more computing devices as described herein, including, for example, the server 110, the first device 120, the second device, the computing device 200, or any combination thereof.

In step 610, a client device (e.g., a client application executing on the client device) may receive a request to create an account. The request to create the account may be associated with a tenant organization. That is, a user, on behalf of a tenant organization, may create an account for the tenant organization. In this regard, the request to create the account for the tenant organization may comprise the organization's name, contact information, and/or a certificate associated with the tenant organization. Additionally or alternatively, a user may request an account associated with the tenant organization. In this regard, the request to create the account may comprise the user's name, a username, a password, contact information (e.g., phone number, email address, etc.), etc. As part of the account creation process, the client device may receive a certificate in step 620. The certificate, which may be stored on a server and accessible to other users, may comprise an affiliation, contact information (e.g., phone number, email address, etc.), a username registered by the user, a public key associated with the user, etc. Alternatively, the client device may generate the certificate in step 620. The certificate may be a self-signing certificate. In this regard, the client device may generate an asymmetric key pair (i.e., a public key and a private key). The public key may be incorporated in the certificate, while the private key may be stored securely on the client device.

Once a client device has created an account, the client device may record data and/or information regarding a resource on a ledger. This data and/or information may include the digital twin of the resource described above with respect to FIGS. 3-5. To record data and/or information to the ledger, the client device may obtain a list of approving devices from a server, in step 630. The client device may send a query to a server. The query may comprise the affiliation or an identifier associated with the tenant organization. The client device may query the server via one or more application programming interfaces (APIs). The server may use the affiliation, or the identifier, to retrieve one or more approving devices associated with the tenant organization. The client device may receive the one or more approving devices from the server, for example, via the one or more APIs.

After obtaining information associated with the one or more approving devices from the server, the client device may create the record, in step 640. The record may comprise at least one of a transaction identifier, a record identifier, and/or an asset identifier. Additionally, the record may comprise parametric and/or molecular data about a resource (e.g., commodity). In this regard, the record may comprise the digital twin described above, a digital DNA-representation of the resource, or a fingerprint of the resource (e.g., commodity) at each change and/or transaction. One or more records associated with the resource (e.g., commodity) may create an ancestry of the movement and/or lifecycle of the resource (e.g., commodity), including, for example, the changes in the chemical, parametric, and/or molecular properties of the resource as it moves, changes, and/or ages. As noted above, the record may comprise a plurality of data and/or information about the resource. For example, the data and/or information may comprise a digital twin of the resource (e.g., exact parameter measurements), a last known holder of the resource, movement and/or location of the resource, historic and back-tested knowledge of the efficiency potential of each parametric element, formula, or content, etc. Upon creation, the record may be flagged as temporary. The record may be flagged as temporary by cloning the record. In some instances, the temporary record may be flagged as temporary when being stored on a private ledger. Additionally or alternatively, the record may be flagged as temporary by encapsulating the record to be written in a temporary record container. Metadata may be appended to the record and/or the temporary record container. The metadata may comprise identifying information (e.g., phone number, email address, username, etc.) associated with each of the one or more approving devices. Additionally or alternatively, the metadata may comprise a unique code for each of the one or more approving devices. The unique code may be a pseudorandom number.

In step 650, the client device may send the record, and the associated metadata to the server. As will be discussed in greater detail below with respect to FIG. 7, the server may send the unique code to each of the one or more approving devices via an electronic communication (e.g., digital message, application programmable interface (API) call, file input, asynchronous data communication, synchronous communication, email communication, push notification, etc.). Alternatively, the client device may provide the unique code and the transaction identifier to each of the one or more approving devices. The client device may provide the unique code and the transaction identifier via an electronic communication, such as a digital message, an API call, file input, asynchronous data communication, synchronous communication, email communication, push notification, an intra-application communication, etc. As will be discussed in greater detail below, the one or more approving devices may use their unique code to verify the record, as discussed in greater detail in FIG. 7. When a threshold number of verifications is satisfied, the server may commit (e.g., write) the record to the ledger (e.g., blockchain). In some examples, committing the record to the ledger includes writing the record to a public ledger or a group of ledgers.

The server may delete, or otherwise remove, any temporary records or clones of the record, including those stored in a private ledger.

It will be appreciated that the method 600 may omit some steps, for example, when updating, changing, modifying, and/or altering an existing record. That is, step 610 and step 620 may be omitted when a client device is updating, changing, modifying, and/or altering an existing record. Similarly, steps 610 and step 620 may be omitted, for example, when a client device is creating a new record after creating an account with the technology platform described herein. In the examples described above, steps 610 and 620 may be replaced with an authentication (e.g., login) procedure.

Figure 7:
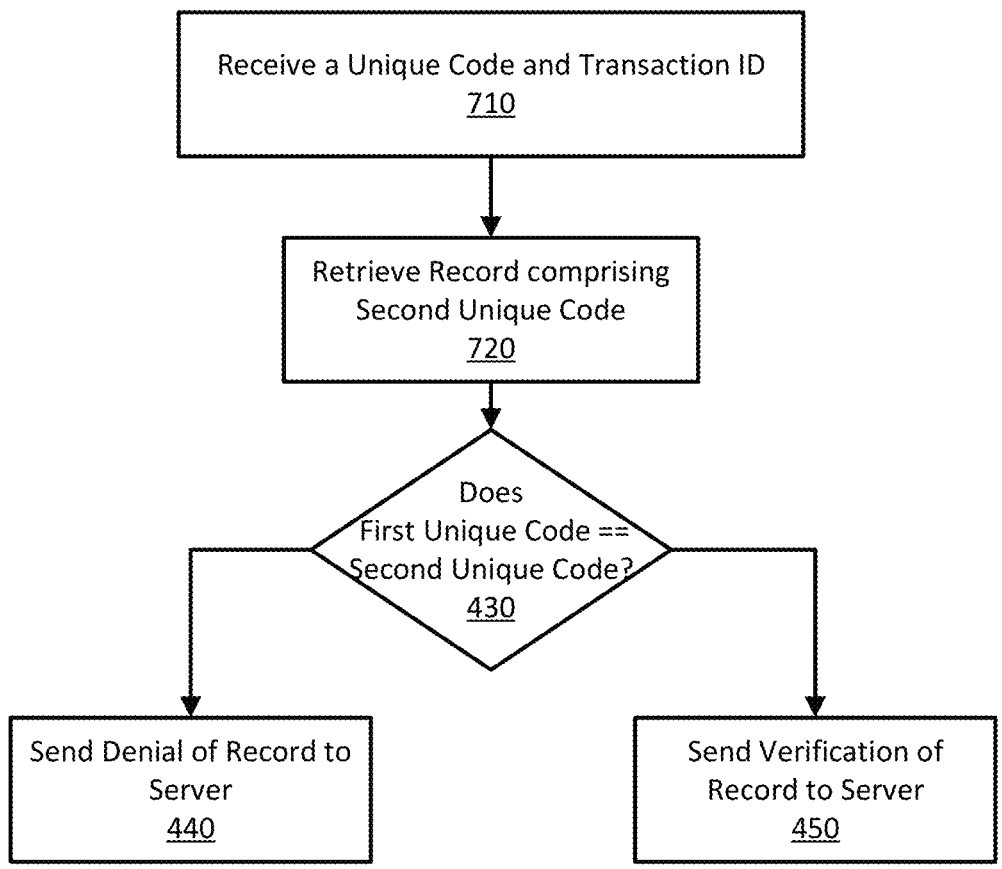
FIG. 7 shows an example of a process for verifying a record in accordance with one or more aspects of the disclosure.

In order for a record to be written to the ledger, the record may need to be verified by one or more users that are authorized to review records before they are written to the ledger. FIG. 7 shows an example of a process 700 for verifying a record in accordance with one or more aspects of the disclosure. Some or all of the steps of process 700 may be performed using one or more computing devices as described herein, including, for example, the server 110, the first device 120, the second device, the computing device 200, or any combination thereof.

In step 710, a client device (e.g., an application executing on the client device) may receive a first unique code and/or a transaction identifier. As noted above, the first unique code and/or the transaction may be received via an electronic communication an electronic communication (e.g., digital message (e.g., text message, SMS, MMS, etc.), application programmable interface (API) call, file input, asynchronous data communication, synchronous communication, email communication, push notification, etc.). Additionally or alternatively, the client device may cause a list of transactions awaiting user approval to be displayed on the client device. In this example, a user may select one or more transactions from the list of transactions. In response to the user's selection, the client device may retrieve the record in step 720. The record may comprise a second unique code. In step 730, the client device may compare the first unique code to the second unique code. If first unique code and the second unique code do not match, the client device may send an indication to the server that the record is denied in step 740. However, if the first unique code and the second code match, the client device may send a verification of the record to the server in step 750.

The verification may comprise invoking a smart contract to approve the record. The verification may comprise two parameters. The first parameter may be a digital signature of a first one-way function (e.g., hash function) of the first unique code, the approving user's username, the record identifier, and/or the asset identifier. The digital signature may be generated with a private key of the approving user. The first one-way function may be SHA-1, SHA-224, SHA-256, SHA-384, SHA-512, SHA-512/224, SHA-512/256, SHA3-224, SHA3-256, SHA3-384, SHA3-512, SHAKE128, SHAKE256, etc. The second parameter may be a result of applying a second one-way function to the transaction identifier and the approving user's username. The second one-way function may be any of the one-way functions described above with respect to the first one-way function.

Figure 8:
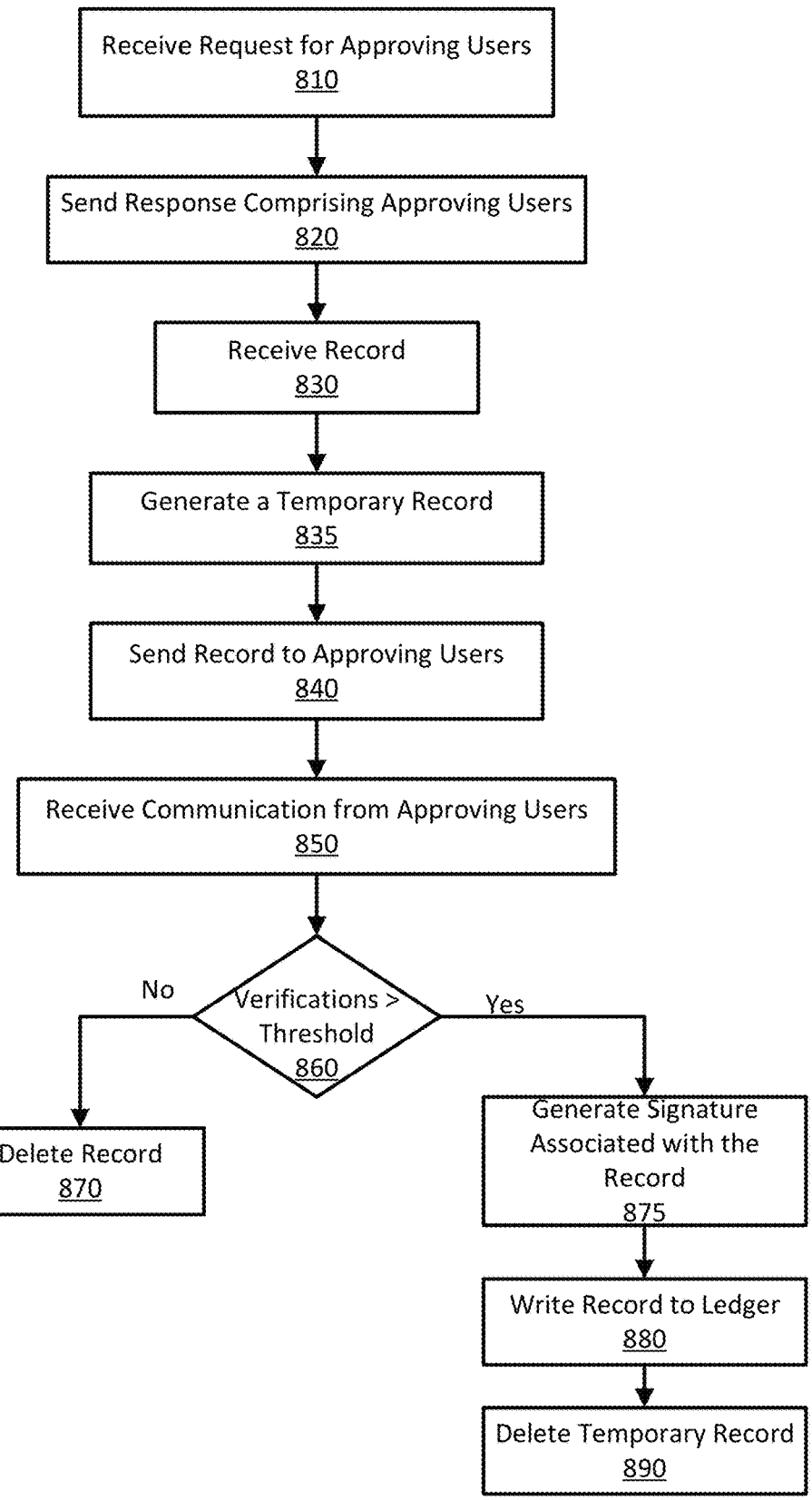
FIG. 8 shows an example of a process of writing a record to a ledger in accordance with one or more aspects of the disclosure.

Once the record is generated and consensus is reached for the record, the record may be written (e.g., committed) to the ledger. FIG. 8 shows an example of a process 800 of writing a record to a ledger (e.g., blockchain, database, immutable database, etc.) in accordance with one or more aspects of the disclosure. Some or all of the steps of process 500 may be performed using one or more computing devices as described herein, including, for example, the server 110, the first device 120, the second device, the computing device 200, or any combination thereof.

In step 810, a server (e.g., an application executing on the server) may receive a request for one or more approving devices. The server may receive the request from a client device (e.g., a client application executing on the client device). The request may comprise an affiliation or identifier associated with a tenant organization that is creating and/or modifying a record. The request may be received via one or more APIs. The server may use the affiliation, or the identifier, to query a database to retrieve one or more records associated with the tenant organization. The one or more records may identify one or more approving devices for the tenant organization. For example, the server may obtain an access control list (ACL) from the tenant organization, and receive identification information of each of the one or more approving devices from the ACL by, for example, querying an API (e.g., a host application API). The identification information may comprise at least one of a phone number, an email address, a username, a user ID, and/or other user identification information for each of the one or more approving devices. Additionally or alternatively, the one or more records may identify a quantity of verifications required to write a record to the ledger.

In step 820, the server may send a response to the request for the one or more approving devices. The response may comprise the identification information for each of the one or more approving devices. The server may send the response to the client device via the one or more APIs.

In step 830, the server, acting as a proxy node, may receive a record of an asset from a client device. As noted above, the record may comprise a transaction identifier, a record identifier, an asset identifier, a unique code for each of the one or more approving devices, and/or identification information for each of the one or more approving devices. The server may determine (e.g., set, change) a state attribute of the record based on receiving the record. For example, based on receiving the record, the server may set a state attribute of the record to be "invoked," and/or set a state attribute of the record to "pending." Additionally or alternatively, the server may change a state attribute of the record from "possibleApprovals" (or similar designation) to a list of the one or more approving devices.

In step 835, the server may generate a temporary record based on the record. The temporary record may be stored in a private ledger, for example, maintained by the transaction platform described herein. The server may, for each of the one or more approving devices on the list, generate a unique code. The unique code may be a pseudorandom number associated with each of the one or more approving devices. The unique code may be a one-time code. Additionally or alternatively, the server may generate two verification parameters for each of the one or more approving devices, for example, in response to receiving the record. The first verification parameter may be a first result of a one-way function (e.g., hash function) applied to a first unique code associated with a first user, first identification information of the first user, and the record identifier. The second verification parameter (e.g., a record key) may be a second result of a one-way function (e.g., hash function) applied to the transaction identifier and the first identification information of the first user. The server may store the first verification parameter and the second verification parameter on the ledger as the temporary record.

Additionally or alternatively, the server may clone the record to create a temporary record. For example, the server may clone the record using a key. The key may be a result of a one-way function (e.g., hash function) applied to the transaction identifier and the first identification information of the first user. The server may add an object to the temporary record's state attribute—"possibleApprovals" (or similar designation). The object may comprise identification information of a user associated with, or otherwise linked to, a first result of a one-way function (e.g., hash function) applied to a unique code associated with the user, the identification information of the user, and the record identifier and a second result of a one-way function (e.g., hash function) applied to the transaction identifier and the identification information of the user.

In step 840, the server may send a record to the one or more approving devices (e.g., a device associated with each of the one or more users authorized to review and/or approve the record). The server may send the record, for example, in response to or based on receiving a request for the record from each of the one or more approving devices. Additionally or alternatively, the server may push the record to the one or more approving devices, for example, in response to the one or more approving devices logging into a client-side application. Additionally or alternatively, the server may send the unique code and information associated with the record (e.g., the entire transaction identifier, or the last several characters of the transaction identifier) to each of the one or more approving devices (e.g., a client device associated with each user authorized to review/approve the record). In this regard, the server may send the unique code and the information associated with the record to each of the one or more approving devices via an external message (e.g., text message, SMS, email communication, push notification, etc.).

A client device (e.g., the client device 120, the application 122) may receive an indication of one or more records that require review. For example, a user (e.g., a user authorized to review/approve) may log in to the application 122 and view a list of pending approvals for one or more records. The list of pending approvals may comprise one or more transaction identifiers. The user may select a record with the transaction identifier matching the information associated with the record received by the user. For example, the user may select a record with a transaction identifier matching the last several (e.g., 6) characters of the received transaction identifier. In this regard, the client device may receive a unique code and a transaction identifier of a record for review. The application 122 may retrieve the record, for example, using the transaction identifier. The record may be retrieved from the server 110, the application 112, a private ledger (e.g., database) (not shown), the ledger 140, or any combination thereof. Upon receiving the record, the client device may compare the unique code with a unique code stored with the record. Additionally or alternatively, the client device may invoke a smart contract by inputting (e.g., sending to the server) two parameters, as described above. For example, the first parameters may be a digital signature of applying a first one-way function (e.g., hash function) to the received unique code, the user's username, and the record identifier. The digital signature may be generated with a private key of the approving user. The second parameter may be a result of applying a second one-way function (e.g., hash function) to the transaction identifier and the user's username. The client device may send a message (e.g., a data packet) comprising the first parameter and the second parameter to the server.

In step 850, the server may receive a communication from each of the one or more approving devices. The communication may comprise the first parameter and the second parameter. Based on the invocation of the smart contract by the user and/or the receiving the message, the server may load the record using a key (e.g., the second parameter received from the client device). The server may verify (e.g., validate) the user's digital signature of the first parameter, for example, using the user's public key. If the digital signature of the first parameter is verified, the server may compare the first verification parameter generated by the server to the result of the user's first one-way function applied to the unique code, the user's username, and the record identifier (e.g., indicating the digital twin of the resource). Similarly, the server may compare the second verification parameter generated by the user to the result of the user's second one-way function applied to the transaction identifier and the user's username. If both of the results of the functions provided by the client device match the first verification parameter and the second verification parameter generated by the server respectively, the record may be deemed verified by the approving user. After being verified, the record may be written to a public ledger (e.g., ledger 140) and deleted from the private ledger. Additionally or alternatively, the record may be committed to a public ledger (e.g., ledger 140) and any clone and/or temporary records stored on the public ledger may be removed (e.g., deleted) after the record has been verified.

Additionally or alternatively, the server may load a cloned record using a key (e.g., the second parameter received from the client device). The server may retrieve an object from the cloned record. For example, the server may retrieve the object based on the "possibleApprovals" (or similar designation) attribute of the record. In this regard, the server may retrieve the "possibleApprovals" (or similar designation) attribute of the record based on a determination that the "possibleApprovals" (or similar designation) attribute of the record matches the identification information of the user. The server may then verify the user's digital signature of the first parameter, for example, using the user's public key. If the digital signature of the first parameter is verified, the server may compare the first verification parameter generated by the server to the result of the user's first one-way function applied to the unique code, the user's username, and the record identifier. If the first verification parameter generated by the server matches the result of the user's first one-way function applied to the unique code, the user's username, and the record identifier, the server may load the cloned record using a key (e.g., the second parameter received from the client device), and authenticate the cloned record. Based on the authentication of the cloned record, the server may copy the cloned record's properties (e.g., information associated with the authentication of the cloned record) to the record.

If one, or both, of the results do not match, the record may not be considered verified by the server, and the record will not be written as confirmed and/or accepted to the ledger (e.g., ledger 140). The verification of both the first verification parameter and the second verification parameter provides two-factor verification for writing records to a ledger. It will be appreciated that step 850 may be applied to any number of responses received from a plurality of the one or more approving devices.

In step 860, the server may determine whether a number of verifications satisfies a threshold. In this regard, a tenant organization may indicate that a predetermined number of approving devices need to verify the record before the record can be written to the ledger. Additionally or alternatively, the threshold may be verified by a predetermined percentage of the approving devices (e.g., more than 50% of the approving devices), or other such approval protocol (e.g., consensus protocol). In some examples, every signed metadata field may be verified by the one or more approving devices of the tenant organization. If the threshold is not satisfied, the server may delete the record in step 870. Alternatively, the server may keep the record pending until a predetermined number of responses have been received or a predetermined amount of time has been passed before deleting the record.

In step 875, if the threshold is satisfied, then the server may sign the record. For example, the server may generate a signature associated with the record, using a private key (e.g., a server private key). The signature may indicate that the record has been approved by a number of approving devices.

In step 880, the server may store the record in the ledger. For example, if the threshold is satisfied, the server may write the record to the ledger (e.g., ledger 140). As noted above, writing the record to the ledger may include writing the record to another ledger (e.g., public ledger) from a private ledger. The server may determine (e.g., set, change, reset) one or more state attributes of the record, based on a determination that the threshold is satisfied. For example, the server may change a state attribute of the record from "pending" to "valid," or "validated" and/or change a state attribute of the record from "possibleApprovals" to "null," and list each one of the one or more approving devices for the record (e.g., "ApprovedBy"=userFTid). In step 890, any temporary records and/or cloned records may be deleted, for example, based on or in response to the record being written to the ledger.

After one or more records are written to the ledger, the server may periodically (e.g., hourly, daily, weekly, monthly, etc.) analyze the records to identify the parties and/or processes, authenticate relationships across a resource's lifecycle, digitally verify data from shared sources, validate compliance with laws and regulations, and/or identify potential fraud. The server (e.g., an application executing on the server) may review the records stored in the ledger on a regular basis (e.g., hourly, daily, weekly, monthly, etc.). The server may then analyze the records to identify records that may present a potential risk. The potential risk may be potential theft, potential fraud, an environmental risk, etc. The analysis performed by the server may comprise one or more of the machine learning models above. When the server identifies one or more risks, the server may generate one or more electronic communications, notifications, alerts, etc.

In one example, a record of 20,000 barrels of nitrogen sulfate may appear in a record in the ledger. The server and/or the one or more machine learning models executing on the server may identify the probable source of the 20,000 barrels of nitrogen sulfate. Additionally or alternatively, the server and/or the one or more machine learning models executing on the server may determine where the 20,000 barrels of nitrogen sulfate where introduced into the supply chain and/or by whom. The server and/or the one or more machine learning models executing on the server may also determine whether the 20,000 barrels of nitrogen sulfate are stolen and/or fraudulent. Based on the analysis, the technology platform may notify the owner of the nitrogen sulfate, the appropriate authorities and/or environmental agencies, etc.

In another example, the technology platform described herein may identify an origin of an oil spill, for example, when a record of the oil spill is recorded in the ledger. In this regard, there may be no report of the spill. However, based on the analysis performed by the server and/or the one or more machine learning models executing on the server, the technology platform may identify the origin (e.g., ship, derrick, etc.) of the oil spill and/or the time oil spent in the environment. Similar to the analysis above, the technology platform may notify the owner of the nitrogen sulfate, the appropriate authorities and/or environmental agencies, etc. to remediate the oil spill.

By capturing and/or collecting the detailed transactional information and parametric information of each discreet transaction/change associated with a resource, the technology platform described herein may create a unique digital DNA or fingerprint of a state in time of the components of the transaction in a process. The technology platform may be able to determine the counterparties of a transaction using the digital DNA, or fingerprint, of the transaction and probabilistic regression analysis of available data (including external sources). The technology platform may be able to validate the counterparties and the transaction through utilization of recording to an immutable record systems (such as blockchain) and the counterparty validation mechanisms therein (e.g., parties accepting the update write to the ledger/database). Moreover, the technology platform described herein may maintain non-validated transactions, or partially validated transactions, in a transaction record system. The non-validated transactions, or partially validated transactions, may be re-analyzed and/or await validation (e.g., wait until completely validated).

One or more aspects discussed herein may be embodied in computer-usable or readable data and/or computer-executable instructions, such as in one or more program modules, executed by one or more computers or other devices as described herein. Generally, program modules include routines, programs, objects, components, data structures, and the like. that perform particular tasks or implement particular abstract data types when executed by a processor in a computer or other device. The modules may be written in a source code programming language that is subsequently compiled for execution, or may be written in a scripting language, such as (but not limited to) Perl, Python, HTML, XSLT, or any suitable scripting language. The computer executable instructions may be stored on a computer readable medium such as a hard disk, optical disk, removable storage media, solid-state memory, RAM, and the like. As will be appreciated by one of skill in the art, the functionality of the program modules may be combined or distributed as desired in various embodiments. In addition, the functionality may be embodied in whole or in part in firmware or hardware equivalents such as integrated circuits, field programmable gate arrays (FPGA), and the like. Particular data structures may be used to more effectively implement one or more aspects discussed herein, and such data structures are contemplated within the scope of computer executable instructions and computer-usable data described herein. Various aspects discussed herein may be embodied as a method, a computing device, a system, and/or a computer program product.

Although certain specific aspects of various example embodiments have been described, many additional modifications and variations would be apparent to those skilled in the art. In particular, any of the various processes described above may be performed in alternative sequences and/or in parallel (on different computing devices) in order to achieve similar results in a manner that is more appropriate to the requirements of a specific application. Thus, embodiments disclosed should be considered in all respects as examples and not restrictive. Accordingly, the scope of the inventions herein should be determined not by the embodiments illustrated, but by the appended claims and their equivalents.

The invention claimed is:

1. A method comprising:
receiving, by a computing device, a record, wherein the record comprises a transaction identifier and identification information for each of one or more approving devices;
generating, by the computing device, a temporary record based on the record;
generating, by the computing device and based on the record, a first verification parameter for each of the one or more approving devices, wherein the first verification parameter comprises a result of a first one-way function applied to: a unique code associated with one of the one or more approving devices, an identifier associated with the one of the one or more approving devices, and a record identifier; and
generating, by the computing device and based on the record, a second verification parameter for each of the one or more approving devices, wherein the second verification parameter comprises a result of a second one-way function applied to the transaction identifier and the identifier associated with the one of the one or more approving devices;
sending, by the computing device and to a device associated with each of the one or more approving devices, the temporary record, the first verification parameter, and the second verification parameter;
receiving, by the computing device and from a quantity of the one or more approving devices, one or more messages, wherein each of the one or more messages comprises an indication of a veracity of the temporary record;
generating, by the computing device and based on a determination that the quantity satisfies a threshold, a signature associated with the record;
storing, by the computing device, the record in a ledger; and
deleting, by the computing device and after the storing the record in the ledger, the temporary record.

2. The method of claim 1, further comprising:
receiving, by the computing device, a request for identifying the one or more approving devices;
determining, based on the request, the identification information of a plurality of approving devices; and
sending, by the computing device, the identification information of the plurality of approving devices.

3. The method of claim 1, wherein the indication of the veracity of the temporary record comprises:
a first parameter corresponding to the first verification parameter; and
a second parameter corresponding to the second verification parameter, and wherein the method further comprises:
verifying the temporary record based on:
the first parameter matching the first verification parameter; and
the second parameter matching the second verification parameter.

4. The method of claim 1, further comprising:
sending, to a device associated with each of the one or more approving devices, a unique code, wherein the indication of the veracity of the temporary record comprises a signature of the unique code.

5. The method of claim 4, further comprising:
verifying the signature of the unique code; and
authenticating, based on verification of the signature, the temporary record.

6. The method of claim 1, wherein sending the temporary record, the first verification parameter, and the second verification parameter comprises:
sending, to the device associated with each of the one or more approving devices, an electronic communication comprising the temporary record, the first verification parameter, and the second verification parameter.

7. The method of claim 1, wherein the ledger comprises a hybrid ledger that is accessible by one or more third parties.

8. A computing device comprising:
one or more processors; and
memory storing instructions that, when executed by the one or more processors, cause the computing device to:
receive a record, wherein the record comprises a transaction identifier and identification information for each of one or more approving devices;
generate a temporary record based on the record;
generate, based on the record, a first verification parameter for each of the one or more approving devices, wherein the first verification parameter comprises a result of a first one-way function applied to: a unique code associated with one of the one or more approving devices, an identifier associated with the one of the one or more approving devices, an asset identifier, or a record identifier; and
generate, based on the record, a second verification parameter for each of the one or more approving devices, wherein the second verification parameter comprises a result of a second one-way function applied to the transaction identifier and the identifier associated with the one of the one or more approving devices;
send, to a device associated with each of the one or more approving devices, the temporary record, the first verification parameter, and the second verification parameter;
receive, from a quantity of the one or more approving devices, one or more messages, wherein each of the one or more messages comprises an indication of a veracity of the temporary record;
generate, based on a determination that the quantity satisfies a threshold, a signature associated with the record;
store the record in a ledger; and
delete, after the storing the record in the ledger, the temporary record.

9. The computing device of claim 8, wherein the instructions, when executed by the one or more processors, cause the computing device to:
receive a request for identifying the one or more approving devices;
determine, based on the request, the identification information of a plurality of approving devices; and
send, to a client device, the identification information of the plurality of approving devices.

10. The computing device of claim 8, wherein the indication of the veracity of the temporary record comprises:
a first parameter corresponding to the first verification parameter; and a second parameter corresponding to the second verification parameter, and wherein the instructions, when executed by the one or more processors, cause the computing device to:
verify the temporary record based on:
the first parameter matching the first verification parameter; and
the second parameter matching the second verification parameter.

11. The computing device of claim 8, wherein the record comprises information indicating at least one of:
an asset identifier,
parametric or molecular data associated with a change of a resource,
a last known holder of the resource,
a location of the resource,
parameter measurements of the resource, or
historic and back-tested knowledge of efficiency potential of each parametric element, formula, or content of the resource.

12. The computing device of claim 8, wherein the ledger is a distributed ledger.

13. The computing device of claim 8, wherein instructions, when executed by the one or more processors, cause the computing device to:
send an electronic communication to the device associated with each of the one or more approving devices, wherein the electronic communication comprises the temporary record, the first verification parameter, and the second verification parameter.

14. The computing device of claim 8, wherein the ledger comprises a hybrid ledger that is accessible by one or more third parties.

15. A non-transitory computer readable medium storing instructions that, when executed, cause:
receiving a record, wherein the record comprises a transaction identifier and identification information for each of one or more approving devices;
generating a temporary record based on the record;
generating, based on the record, a first verification parameter for each of the one or more approving devices, wherein the first verification parameter comprises a result of a first one-way function applied to: a unique code associated with one of the one or more approving devices, an identifier associated with the one of the one or more approving devices, and an asset identifier; and
generating, based on the record, a second verification parameter for each of the one or more approving devices, wherein the second verification parameter comprises a result of a second one-way function applied to the transaction identifier and the identifier associated with the one of the one or more approving devices;
sending, to a device associated with each of the one or more approving devices, the temporary record, the first verification parameter, and the second verification parameter;
receiving, from a quantity of the one or more approving devices, one or more messages, wherein each of the one or more messages comprises an indication of a veracity of the temporary record;
generating, based on a determination that the quantity satisfies a threshold, a signature associated with the record;
storing the record in a ledger; and
deleting, after the storing the record in the ledger, the temporary record.

16. The non-transitory computer readable medium of claim 15, wherein the instructions, when executed, further cause:
receiving a request for identifying the one or more approving devices;
determining, based on the request, the identification information of a plurality of approving devices; and
sending the identification information of the plurality of approving devices.

17. The non-transitory computer readable medium of claim 15, wherein the indication of the veracity of the temporary record comprises:
a first parameter corresponding to the first verification parameter; and
a second parameter corresponding to the second verification parameter.

18. The non-transitory computer readable medium of claim 15, wherein the record is associated with a fungible good.

19. The non-transitory computer readable medium of claim 15, wherein instructions, when executed, cause:
sending, to the device associated with each of the one or more approving devices, an electronic communication comprising the temporary record, the first verification parameter, and the second verification parameter.

20. The non-transitory computer readable medium of claim 15, wherein the ledger comprises a hybrid ledger that is accessible by one or more third parties.

* * * * *